(12) United States Patent
de Malibran-Santibanez et al.

(10) Patent No.: US 11,173,022 B2
(45) Date of Patent: Nov. 16, 2021

(54) LIQUID APPLICATOR FOR DELIVERING VACCINES

(71) Applicant: BOEHRINGER INGELHEIM ANIMAL HEALTH USA INC., Duluth, GA (US)

(72) Inventors: Aurelie de Malibran-Santibanez, Atlanta, GA (US); Alonso Prado-Masias, Peachtree Corners, GA (US); Frederic David, Watkinsville, GA (US)

(73) Assignee: BOEHRINGER INGELHEIM ANIMAL HEALTH USA INC., Duluth, GA (US)

(*) Notice: Subject to any disclaimer, the term of this patent is extended or adjusted under 35 U.S.C. 154(b) by 36 days.

(21) Appl. No.: 15/895,876

(22) Filed: Feb. 13, 2018

(65) Prior Publication Data
US 2019/0021831 A1    Jan. 24, 2019

Related U.S. Application Data

(60) Provisional application No. 62/458,428, filed on Feb. 13, 2017.

(51) Int. Cl.
| | | |
|---|---|---|
| *A61D 1/02* | (2006.01) |
| *A61J 1/06* | (2006.01) |
| *A61D 7/00* | (2006.01) |
| *A61J 1/20* | (2006.01) |
| *A61K 39/02* | (2006.01) |
| *A61M 3/00* | (2006.01) |
| *A61K 39/10* | (2006.01) |
| *A61K 39/00* | (2006.01) |

(52) U.S. Cl.
CPC ............... *A61D 1/025* (2013.01); *A61D 7/00* (2013.01); *A61J 1/067* (2013.01); *A61J 1/2096* (2013.01); *A61K 39/099* (2013.01); *A61M 3/005* (2013.01); *A61K 2039/10* (2013.01); *A61K 2039/54* (2013.01)

(58) Field of Classification Search
CPC .. A61D 1/025; A61D 7/00; A61J 1/067; A61J 1/2096; A61M 3/005; A61M 3/02; A61K 39/099; A61K 2039/54; A61K 2039/10
See application file for complete search history.

(56) References Cited

U.S. PATENT DOCUMENTS

| | | | | |
|---|---|---|---|---|
| 2,197,689 | A * | 4/1940 | Fromm ................. | A61M 31/00 604/213 |
| 3,325,059 | A * | 6/1967 | Hein ..................... | B65D 47/18 222/207 |
| 3,993,223 | A * | 11/1976 | Welker, III ........... | B65D 1/095 222/107 |
| 4,795,444 | A * | 1/1989 | Hasegawa .............. | A61M 3/00 604/218 |
| D358,466 | S * | 5/1995 | Harris ......................... | D24/115 |
| 6,328,715 | B1 * | 12/2001 | Dragan ................... | A23G 9/24 604/232 |
| 6,544,213 | B1 | 4/2003 | Lifshey | |

(Continued)

*Primary Examiner* — Theodore J Stigell
(74) *Attorney, Agent, or Firm* — Jamie L. Graham; John Ezcurra

(57) ABSTRACT

The invention relates to a liquid applicator, for administering liquids, including vaccines, to animals. In particular, the applicator is useful for delivering liquids to mouths of animals.

24 Claims, 4 Drawing Sheets

(56) References Cited

U.S. PATENT DOCUMENTS

| | | | | |
|---|---|---|---|---|
| 2004/0086582 A1* | 5/2004 | Mitchell | ............... | A23F 3/163 |
| | | | | 424/756 |
| 2007/0292367 A1* | 12/2007 | Clarot | ............... | A61C 19/063 |
| | | | | 424/52 |
| 2009/0136543 A1* | 5/2009 | Ballou | ............... | A61P 37/00 |
| | | | | 424/206.1 |
| 2009/0269121 A1* | 10/2009 | Snedden | ............ | A61C 17/0202 |
| | | | | 401/183 |
| 2010/0198147 A1* | 8/2010 | Perovitch | ............... | A61J 1/067 |
| | | | | 604/77 |
| 2011/0160677 A1* | 6/2011 | March | ............... | A61J 1/067 |
| | | | | 604/212 |
| 2015/0182619 A1 | 7/2015 | Tucker | | |

* cited by examiner

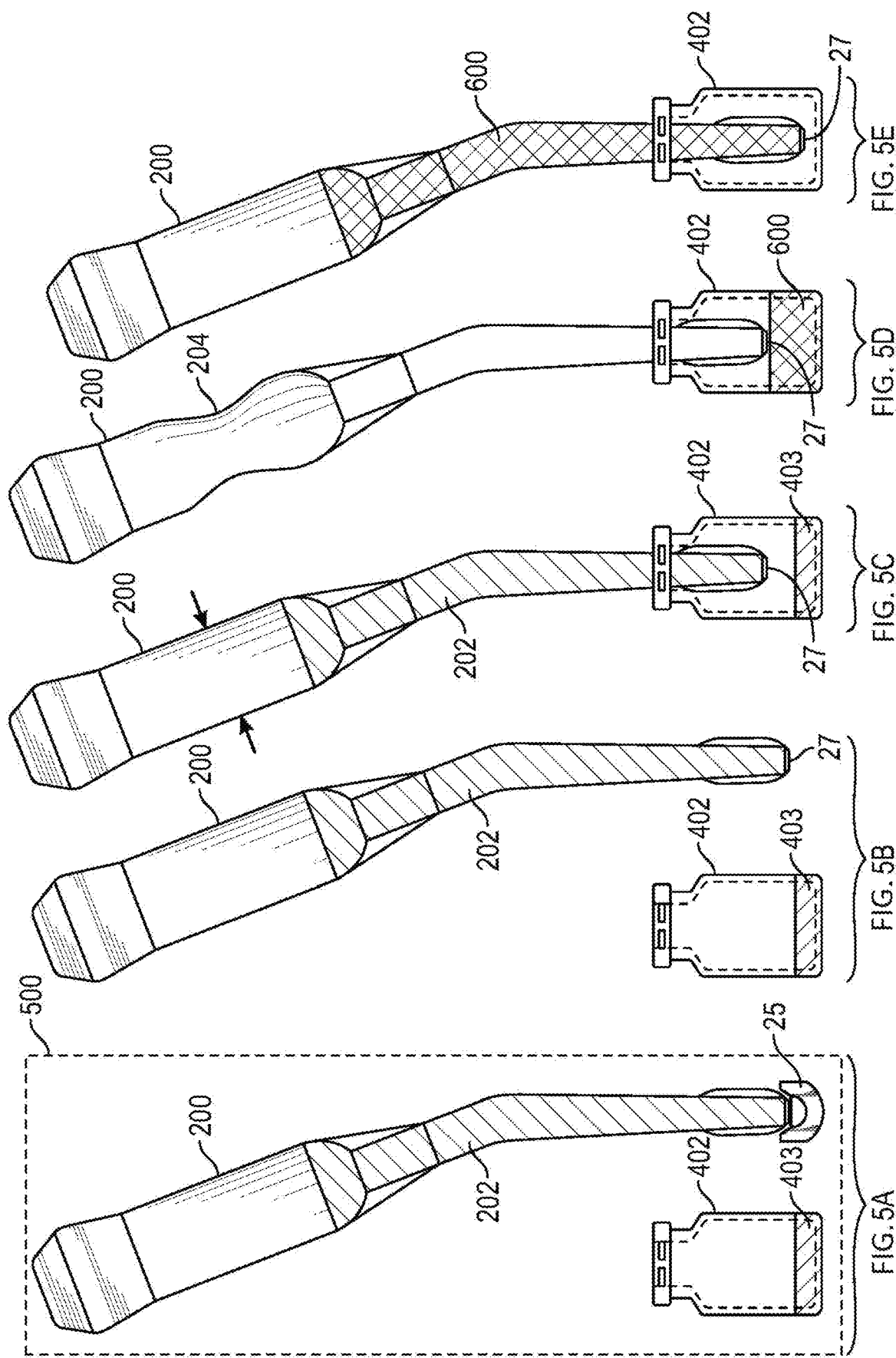

LIQUID APPLICATOR FOR DELIVERING VACCINES

CROSS REFERENCE TO RELATED APPLICATIONS

This application claims the benefit of priority to U.S. Provisional Patent Application No. 62/458,428 filed on Feb. 13, 2017, which is incorporated herein by reference in its entirety.

FIELD OF THE INVENTION

The invention relates to a liquid applicator and methods of use for delivering formulations, including vaccines, to animals.

BACKGROUND OF THE INVENTION

Disposable devices, including syringes, pipettes and other such applicators, are currently used to deliver fluids to the mouths and noses of animals. Unfortunately, existing devices are not well-designed to provide safe and effective vaccination. Applicants thus sought to develop an improved, ergonomic, liquid applicator, which contains an angled or flexible stem, which can deliver fluids, including vaccines, safely and effectively to animals in need thereof.

SUMMARY OF THE INVENTION

The disclosure is based upon the successful engineering of a liquid applicator for delivering liquid formulations to animals. In an aspect, the disclosure provides an improved device for the rapid oral administration of vaccines or other pharmaceutical agents to animals, including canine and feline animals, including puppies and kittens. The applicator may be pre-filled with sterile carrier liquid, which may include but not be limited to water, surfactants, adjuvants, preservatives, and other non-immunogen, and/or pharmaceutically and/or veterinarily acceptable excipients. In other embodiments, the applicator is not pre-filled and may be used to dispense vaccines or other pharmaceutical active agents that are in the form of a liquid solution, emulsion or suspension. In one embodiment, to use the applicator, a user opens the applicators and dispenses or pours carrier liquid into a vial containing lyophilized immunogens. The user then blends the liquid with the immunogens, and draws the resulting liquid formulation back into the applicator by compressing and releasing the applicator's resilient reservoir. Finally, the user inserts the formulation-loaded applicator into the mouth of an animal to be vaccinated, compresses the resilient reservoir, thereby administering the liquid formulation to the animal. In other embodiments, the liquid applicator may be used to administer a liquid medicament to animals via other routes of administration (e.g. topical, nasal, ocular, otic, among others).

The disclosure includes a method of vaccinating an animal in need there of comprising administering a liquid vaccine to the animal; e.g., using a kit. Such a kit is found to increase the safety of the animal and the person administering the vaccine to the anima. Such a method, applicator and/or kit is found to reduce the anxiety of an animal in need of vaccination while receiving the vaccination.

BRIEF DESCRIPTION OF THE DRAWINGS

FIG. 5A is a schematic of a kit for oral vaccination 500 comprising an applicator with carrier liquid and a vial containing lyophilized immunogen.

FIG. 5B is an illustration of kit of FIG. 5A after opening the kit and removing a seal from the distal end of the applicator.

FIG. 5C is an illustration of the distal end of the applicator of FIG. 5B inserted into the vial.

FIG. 5D is an illustration of the carrier liquid of FIG. 5C forced into the vile and admixed with the lyophilized immunogen to form a blended vaccine formulation.

FIG. 5E is an illustration of the blended vaccine formulation in the applicator.

DETAILED DESCRIPTION OF THE INVENTION

Figure 1A:
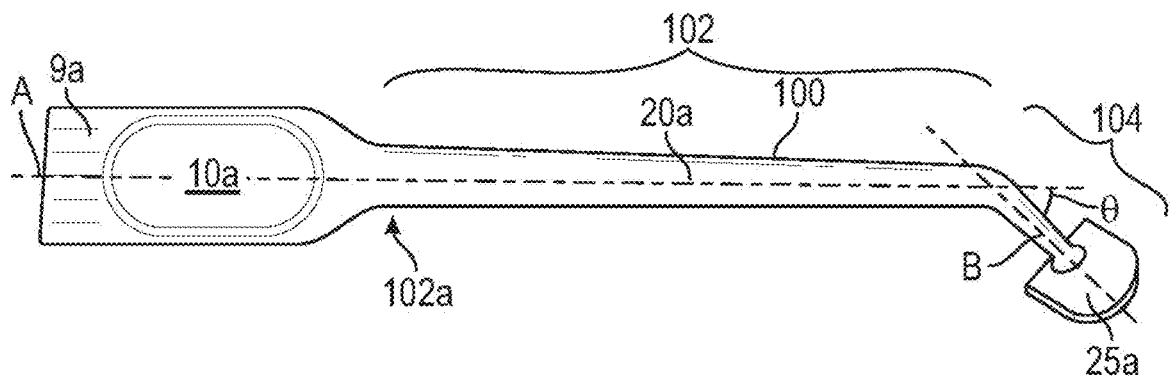
FIG. 1A is a side view of an embodiment of the liquid applicator.

With reference to the figures, embodiments are described with regard for the best mode and preferred embodiment. In a general sense, the description includes a pipette-type liquid applicator 100/200/300 for administering liquid formulations, including vaccine formulations, to animals, e.g., per os. The applicator 100/200/300 includes at least one resilient reservoir 10a/10b/10c and stem 20a/20b/20c for drawing a liquid into the applicator and expelling a liquid, e.g., a blended vaccine formulation 600 from the applicator. In an embodiment, the blended vaccine formulation may comprise one or more lyophilized immunogens. Once the applicator is opened via removal of a seal, e.g., seal 25a/25b or seal 12, a carrier liquid 202 may be poured or dispensed into vial 400/402 containing one or more lyophilized immunogens 403, e.g., a vaccine component. Once the carrier liquid 202 is sufficiently blended with the lyophilized immunogen 403, e.g., the vaccine component, to form a blended vaccine formulation 600, the resilient reservoir 10a/10b/10c is compressed by squeezing (e.g., 204) to generate suction to draw up the blended vaccine formulation, re-inserted into the vial, and the reservoir released. Due to the resulting vacuum, the formulation is thereby urged through the distal opening 27 of the stem 20a/20b/20c and into the reservoir 10a/10b/10c. In an embodiment, the combined volume of the reservoir 10a/10b/10c and stem 20a/20b/20c is large enough to accommodate and/or deliver at least one dose of blended vaccine formulation 600 to an animal per os. After the blended vaccine formulation 600 is loaded into the applicator 100/200/300, the distal end e.g., 27 is inserted into the mouth of an animal to be vaccinated, and the reservoir 10a/10b/10c is compressed to deliver the formulation into the mouth of the animal, e.g., a buccal surface, or buccal cavity thereof.

In an embodiment, with reference to FIG. 1A, applicator 100 comprises hollow stem 20*a* in fluid communication with reservoir 10*a*. Stem 20*a* is bounded at a distal end by frangible seal 25*a*. Tab 9*a* bounds the reservoir end of the applicator. Stem 200*a* further comprises a bend and two linear stem regions 102 and 104. In an embodiment, the stem regions 102, 104, defining axes A and B respectively may intersect to form angle theta (θ). In an embodiment the stem regions 102, 104 may have a length ratio of from 10:1 to 1:10; or from 5:1 to 1:5 or from 3:1 to 1:3; or from 1:2 to 2:1.

Figure 1B:
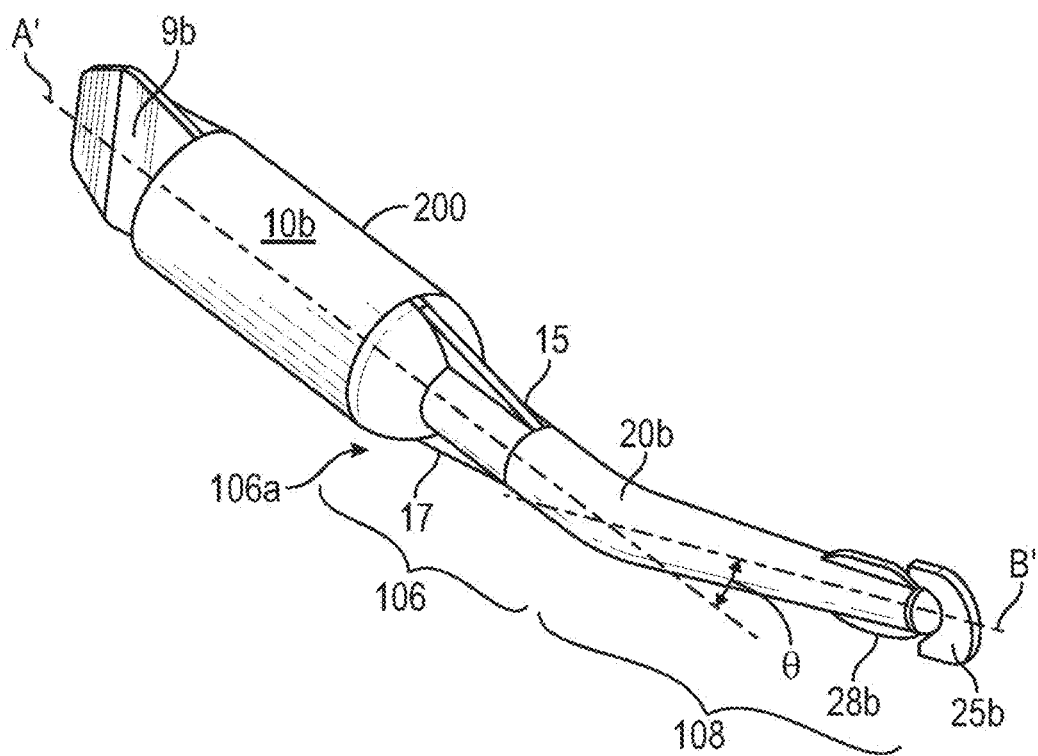
FIG. 1B is a perspective view of a second embodiment of the liquid applicator.

In an embodiment, with reference to FIG. 1B, applicator 200 comprises hollow stem 20*b* in fluid communication with reservoir 10*b*. Stem 20*b* is bounded at a distal end by frangible seal 25*b*. Graspable tab 9*b* bounds the reservoir 10*b* end of applicator 200. Stem 20*b* further comprises a bend and two linear stem regions 106 and 108. In an embodiment the stem regions 106, 108, defining axes A' and B' respectively may intersect to form angle theta (θ). Stem regions 106, 108 may have a length ratio of from 10:1 to 1:10; or from 5:1 to 1:5 or from 3:1 to 1:3; or from 1:2 to 2:1. In an embodiment, stem region 106 may further comprise one or more longitudinal stiffeners 15, 17. Longitudinal stiffeners 15 and 17, that in part join stem 20*b* to reservoir 10*b*, may be adapted to allow stem 20*b* to resist deformation during applicator 100 use. In an embodiment, diametrically disposed tabs 28*a* and 28*b* provide a support surface for a user to grasp while removing seal 25*b*. Tabs 28*a*, 28*b* may allow distal end 27 to remain fully opened and resist deformation during use. Tab 9 (e.g., formed by thermosealing of the reservoir) may be grasped by a user, for example, to avoid prematurely dispensing vaccine (i.e. prior to achieving optimal placement in the animal's mouth).

Figure 4A:
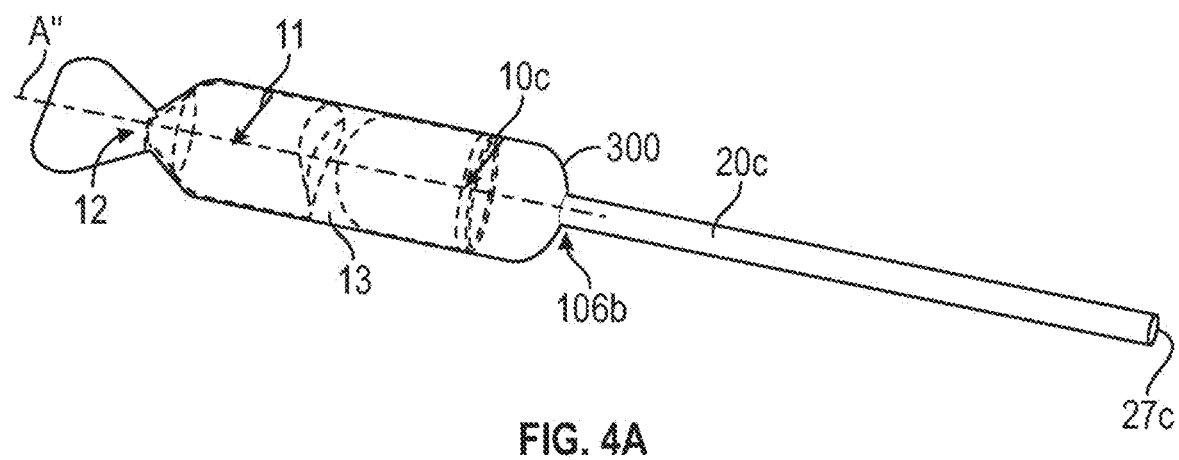
FIG. 4A is a perspective view of a third embodiment having one reservoir for containing liquid carrier and another reservoir for drawing up and administering liquid formulation.
Figure 4B:
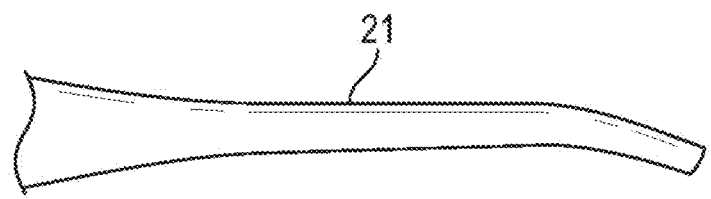
FIG. 4B is an alternative configuration for the distal end of the stem shown in FIG. 4A.

In another embodiment, with respect to FIG. 4A, applicator 300 comprises hollow stem 20*c* in fluid communication with reservoir 10*c*. Stem 20*c* is bounded at a distal end 27*c*. Applicator 300 may comprise separate, e.g., separated reservoirs 11, wherein reservoir 11 contains a liquid carrier. Reservoir 10*c* is resilient, and functions as an elastic suction bulb. In this embodiment, a seal at the distal end 27 of stem 20*c* may be omitted, since the first reservoir 11 has its own frangible seal 12. In other words, only one seal is required for retaining the carrier liquid within the applicator as provided to the user. As is visible in FIG. 4A, sealing region 13 defines a barrier between reservoirs 10*c* and 11.

In both the single and multi-reservoir embodiments, application of mechanical force (e.g. a user squeezing thumb and finger around the reservoir) expels liquid contents, and release of mechanical force (e.g. user releasing thumb and finger from around the reservoir) generates the suction required to draw up the liquid.

In some embodiments, the applicator may comprise fused dual or double stems 20, e.g., to provide a stiffer stem 20 while, e.g., concomitantly decreasing residual volume of liquid formulation.

The embodiments of the description include one or more of the following.

Embodiment 1 may be an applicator 100/200/300, e.g., for containing, e.g., sealably containing, a carrier liquid 202 and for delivering a veterinarily acceptable nutraceutical, pharmaceutical or biological formulation 600 to an animal in need thereof, the applicator comprising:

a resilient and/or elongated reservoir 10*a*/10*b*/10*c*, defining a longitudinal axis A/A'. an elongate, angled, hollow stem 20*a*/20*b*/20*c*, adapted to be inserted into the animal's mouth, the stem 20*a*/20*b*/20*c* comprising proximal (102*a*/106*a*) and distal ends (e.g., 104/108/27), the proximal end 102*a*/106*a* operably connected to and in fluid communication with the reservoir 10*a*/10*b*/10*c*, and distal end (e.g., 104/108/27) serving as a conduit through which a liquid exits and enters the applicator;

wherein the applicator is adapted to sealably contain a carrier liquid 202 to be dispensed;

and adapted to dispense the carrier liquid 202 upon the application of mechanical pressure to the reservoir 10*a*/10*b*/10*c*, and adapted to draw the liquid back into the reservoir when the mechanical pressure is first applied to the reservoir and then released while the reservoir is in fluid communication with a liquid 600; and Embodiment 1 may also comprise a frangible seal 25*a*/25*b* wherein exit and entry of fluid from the applicator is blocked until the frangible seal is broken.

Embodiment 1 may also comprise an applicator 100/200/300 adapted to deliver a liquid composition to an animal per os, comprising a resilient and/or elongated reservoir defining a longitudinal axis, an elongate, angled, hollow stem adapted to be inserted into the animal's mouth, the stem comprising proximal and distal ends, the proximal end operably connected to and in fluid communication with the reservoir and the distal end adaptable to allow liquid to exit and enter the applicator; and wherein the applicator is adapted to sealably contain a carrier liquid of the liquid composition to be dispensed to the animal.

Embodiment 2 may comprise an applicator 300 for sealably containing a carrier liquid and for delivering a veterinarily acceptable nutraceutical, pharmaceutical or biological formulation to an animal in need thereof, the applicator comprising at least a first reservoir defining an axis A", adapted to contain a carrier liquid to be dispensed; at least a second reservoir 10*c*, the second reservoir 10*c* optionally coaxial with the first reservoir, resilient and elongated, and adapted to draw liquid into the second reservoir 10*c* when mechanical pressure is first applied to the second reservoir 10*c* and then released while the second reservoir is in fluid communication with the liquid;

an elongated, optionally angled, hollow stem 20*c*, adapted to be inserted into the animal's mouth, the stem 20*c* comprising proximal 106*b* and distal 27*c* ends, the proximal end 106*c* operably connected to and capable of fluid communication with the second reservoir 10*c* and not the first reservoir, and the distal end 27*c* defining a conduit through which the liquid exits and enters the applicator.

Embodiment 2 may comprise a first frangible seal 12 wherein fluid exit of the liquid from the first reservoir is blocked until a first frangible seal 12 is broken.

Embodiment 3 may comprise the applicator of embodiment 1, wherein a portion of the stem defines an axis B/B' and the axis is angled to an angle theta (θ) wherein theta is from about 0 to about 40 degrees, with respect to the longitudinal axis A/A'.

Embodiment 4 may comprise the applicator of embodiment 2, wherein the stem is angled to an angle theta (θ) wherein theta is from about 0 to about 40 degrees, with respect to the longitudinal axis A/A'.

Embodiment 5 may comprise the applicator of embodiment 3 or 4, wherein theta is from about 0 to about 35, or from about 15 to about 35, about 20 to about 30 degrees, or about 25 degrees.

Embodiment 6 may comprise the applicator of embodiment 3, wherein the distal end of the stem is sealed by a frangible seal 25*a*/25*b*.

Embodiment 6 may further comprise the frangible seal 25*a*/25*b* breakable by a twisting or torqued force.

Embodiment 7 may comprise the applicator of embodiment 4, wherein the distal end of the first reservoir 11 is sealed by a frangible sealing means 12 configured to be broken, e.g., by a twisting motion or torque, thereby permitting the liquid to be poured out of the applicator.

Embodiment 8 may comprise the applicator of embodiment 3, wherein the stem is for suction of liquids by vacuum created by compressing the resilient reservoir and thereafter gradually releasing the compression of the resilient reservoir.

Embodiment 8 may further comprise the stem in fluid communication with, and is substantially in airtight connection with, the reservoir, once the sealing means is broken.

Embodiment 9 may comprise the applicator of embodiment 5, wherein an inside surface of the resilient reservoir and stem are smooth and without projections or depressions.

Embodiment to may comprise the applicator of embodiment 5, wherein a transition between an inside surface of the resilient reservoir and an inside surface of the stem is smooth and without edges.

Embodiment 11 may comprise the applicator of embodiment 5, wherein the stem angle is optimized to reduce the amount of residual blended vaccine formulation after a single compression of the resilient reservoir.

Embodiment 12 may comprise the applicator of embodiment 5, wherein less than about 10% to about 20% (v/v) of the blended vaccine formulation remains in the resilient reservoir after a single compression of the resilient reservoir.

Embodiment 13 may comprise the applicator of embodiment 12, wherein less than about 15% (v/v) of the formulation remains in the resilient reservoir after two compressions of the resilient reservoir.

Embodiment 14 may comprise the applicator of embodiment 4, wherein the first reservoir and second reservoir are not in fluid communication with one another, and are blow-molded from a single piece of polymeric material.

Embodiment 15 may comprise the applicator of embodiment 4, wherein the first reservoir is resilient enough to be compressed, but not so resilient that when the frangible sealing means is broken, the mere holding force causes the liquid contained within the first reservoir to be expelled.

With respect, for example, to FIG. 5, embodiment 16 may comprise a method of vaccinating an animal in need thereof comprising the steps of:

providing an applicator (100/2000/300) according to any one of the proceeding embodiments;

breaking at least one sealing means (25a/25b/12), e.g., to allow a liquid carrier to be dispensed from the applicator;

optionally inserting the distal end (104/108/27) into the vial 402;

dispensing the liquid carrier into a vial (402) containing lyophilized immunogen 403; blending the liquid carrier and the lyophilized vaccine to produce the desired solution or suspension 600;

optionally removing the distal end from the vial;

compressing the resilient reservoir 10a/10b/10c (e.g., to position 204);

optionally ensuring that the distal end of the stem is open to the external environment; inserting the open distal end into the vial such that the distal end is in fluid communication with the now blended vaccine formulation 600;

releasing the compression (204) of the resilient reservoir, thereby drawing up the blended vaccine formulation through the stem 20a/200b/20c and into the resilient reservoir 10a/10b/10c;

inserting the distal end (27) of the applicator into the mouth of the animal to be vaccinated;

compressing the resilient reservoir to apply the blended vaccine formulation inside the mouth of the animal.

The present invention also encompasses any of the embodiments 1 to 15 described above wherein the applicator of the invention is used administering a liquid solution, suspension or emulsion containing a vaccine or pharmaceutical agent that does not require reconstitution with water or another liquid to an animal in need thereof. In this alternate embodiment, the applicator is not pre-filled with a reconstituting liquid and the liquid, suspension or emulsion containing the vaccine or pharmaceutical agent in a vial or other container is directly drawn into the empty applicator for subsequently administering the solution to the animal.

It will also be appreciated that the present invention encompasses administration of a vaccine or other pharmaceutical agent in the form of a liquid solution, suspension or emulsion to an animal via other routes of administration including, but not limited to, topical administration (to the skin), ocular administration, otic administration (via ear), nasal administration, rectal or vaginal administration, or by inhalation.

With respect, for example, to FIG. 5A, 5B, 5C, 5D, 5E, an alternative embodiment 16 may comprise a method of vaccinating an animal in need thereof comprising the steps of:

providing an applicator 100/200 breaking the frangible seal 25a/25b e.g., to allow a liquid carrier 202 to be dispensed from the applicator;

optionally inserting the distal end 104/108/27 into a vial 400/402 containing lyophilized immunogen 403;

dispensing the liquid carrier into the vial;

sufficiently blending the liquid carrier and the lyophilized immunogen to produce a blended vaccine formulation;

optionally removing the distal end;

compressing the resilient reservoir;

optionally ensuring that the distal end of the stem is open to the external environment;

inserting the open distal end into the vial such that the distal end is in fluid communication with the blended vaccine formulation;

releasing the compression of the resilient reservoir, thereby drawing up the blended vaccine formulation through the stem, and optionally, into the resilient reservoir;

inserting the distal end into the mouth of the animal to be vaccinated;

compressing the resilient reservoir to administer the blended vaccine formulation inside the mouth of the animal.

Embodiment 17 may comprise the method of embodiment 16, wherein the applicator has only one reservoir, which serves the multiple purposes of: containing the carrier liquid, dispensing the carrier liquid into the vial, drawing up the vaccine formulation into the applicator, and finally, delivering the vaccine formulation to the animal.

Embodiment 18 may comprise the method of embodiment 16, wherein there are only two reservoirs:

a first reservoir for containing and dispensing the liquid carrier; and a second reservoir for drawing up and expelling blended vaccine formulation.

Embodiment 19 may comprise the method of any one of embodiments 16 to 18, wherein the animal is a canine and the vaccine comprises a protective immunogen capable of providing the canine with protective immunity against a rabies virus or a *Bordetella*; or alternatively, a pathogen selected from the group consisting of an influenza virus, a parainfluenza virus, a canine influenza virus, a bordatella virus, a rabies virus a parvovirus, an adenovirus, and a distempter virus.

Embodiment 20 may comprise the method of embodiment 19, wherein one vaccination is protective in the canine for at least 1 year, or at least 3 years, or from 0.5 years to about 1 year, or from about 0.5 years to about 2 years, or from about 0.5 years to about 3 years.

Embodiment 21 may comprise a kit 500 comprising an applicator 100/200/300 and a sealed vial 400/402 comprising a lyophilized immunogen.

Applicator Production.

The applicator may generally be produced according to the following steps: 1) Blow Fill Seal; 2) printing or labelling; and 3) packaging (e.g. bags of 25). The sealed reservoir may be pre-filled with water and suitable, e.g., veterinarily acceptable, excipients. In some embodiments, a 1.0 ml dose is recoverable from the applicator, taking in account: residual volume in 3 cc vial and tube, any loss while opening the tip (splashing), any water loss/intake through the tube walls and through the entire shelf-life of liquid carrier (e.g. diluent; 36 months). In some embodiments, the estimated filling volume of the applicator may be from about 1 mL to about 3 mL, or from about 1.1 mL to about 2.5 mL, or from about 1.2 to about 2.0 mL, or from about 1.3 mL to about 1.8 mL, or from about 13 to about 14 mL.

In other embodiments for delivering larger volumes, the filling volume of the applicator may be from about 2 mL to about to mL, from about 2 mL to about 8 mL or from about 3 mL to about 6 mL. In other embodiments, the filling volume of the applicator may be larger than about to mL including from about to mL to about too mL, from about to mL to about 80 mL or from about to mL to about 50 mL. In yet other embodiments, the fill volume of the applicator may be from about 20 mL to about 50 mL, from about 30 mL to about 50 mL or from about 40 mL to about 50 mL The applicator may be made of any suitable material, including but not limited to LDPE, MDPE and HDPE.

The amount of dry material to be reconstituted with liquid will depend on the dose to be administered. Accordingly, various dosages may be administered with applicators having different fill volumes. In some embodiments, the amount of dry material (e.g. lyophilized material) in the vial or other container which is reconstituted with liquid prior to dispensing may be from about 0.01 grams to about 5 grams or more. More typically, the weight of the material to be reconstituted may be from about 0.01 grams to about 1 gram or from about 0.01 grams to about 0.5 grams. In other embodiments, the weight of dry material that will be reconstituted will be from about 0.01 grams to about 0.25 grams or from about 0.05 grams to about 0.15 grams. In yet another embodiment, the amount of dry material that is reconstituted with liquid is about 0.1 grams.

Advantages

In some embodiments, the applicator is intuitive and easy to open for adults, including veterinarians. In some embodiments, no sharp edges are created during removal of the tip/seal.

Figure 2:
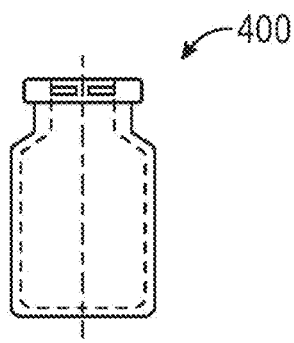
FIG. 2 is a side view showing a vial into which a carrier liquid is added and from which an applicator is inserted to draw up a blended liquid formulations.
Figure 3A:
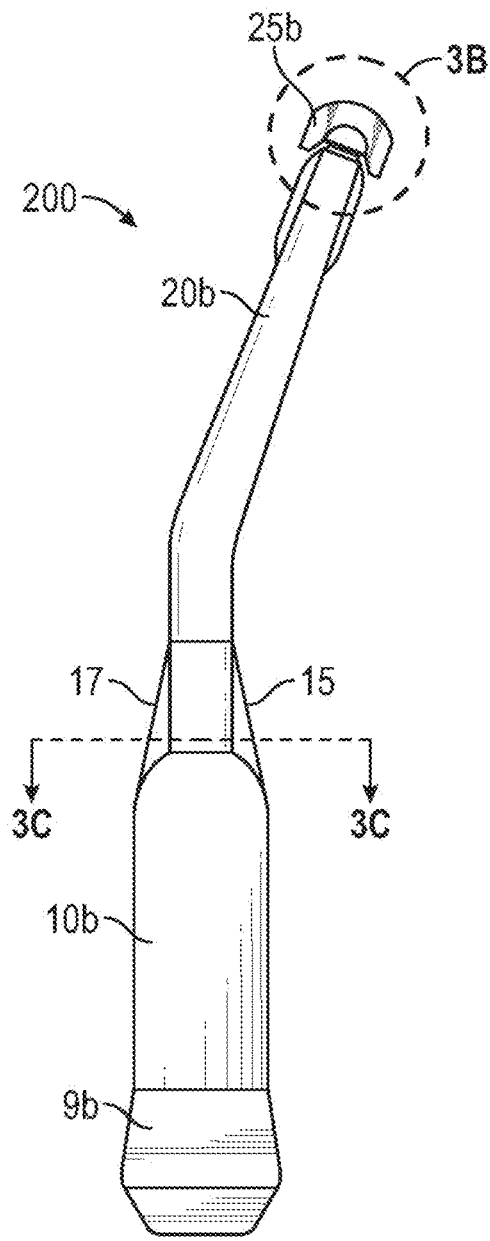
FIG. 3A is a side view illustrating the second embodiment of FIG. 1B of the applicator.
Figure 3B:
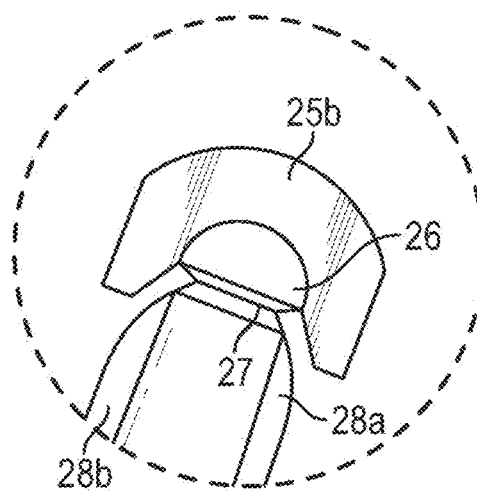
FIG. 3B is an expanded view of a portion of FIG. 3A.
Figure 3C:
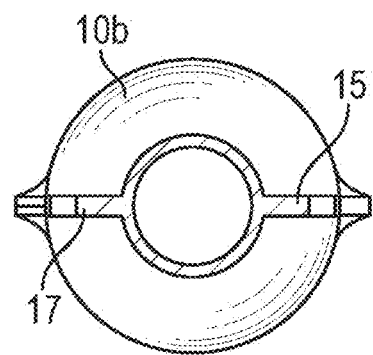
FIG. 3C is a cross sectional view of along line 3C of FIG. 3A.

In some embodiments, the applicator is adapted to allow the user to dispense into and then withdraw from a 3 cc vial. As indicated in FIG. 2, the applicator should be able to be inserted into a vial having the following dimensions (in inches):

A) Crown O.D. about 0.517
B) Neck Depth about 0.030R MIN.
C) Neck I.D. about 0.277
D) Overall Height about 1.484
E) Neck Height about 0.181
F) Crown Height about 0.154
G) Body Wall Thickness about 0.043
H) Body Diameter about 0.659
T) Top Height about 0.335

In some embodiments, the applicator may deliver a dose of the blended vaccine formulation 600 with one (1) squeeze or at most two (2) squeezes. Residual volumes, e.g., the volume of formulation 600 remaining after application to the animal's mouth, are kept to a minimum, for example, less than about 15% of the original volume of formulation 600, or less than about 14%, or less than about 13%, or less than about 12%, or less than about 11%, or less than about 10%, or less than about 9%, or less than about 8%, or less than about 7%, or less than about 6%, or less than about 5%, or less than about 4%, or less than about 3%, or less than about 2% or less than about 1% residual volume. In some embodiments, two squeezes leave less than about 4% residual volume and 1 squeeze leaves less than about 15%.

In some embodiments, the applicator stem is designed to complement the shape of the mouth of the animal to be vaccinated. For example, a long stem can improve ergonomics and facilitate administration. In some embodiments, a long stem with appropriate flexibility, or a long gently angled stem may be employed.

In some embodiments, the applicator, particularly once the seal has been broken, may be used to administer vaccines to animals using only one hand. This applicator feature allows the user to hold and coax the animal with one hand/arm, while administering vaccine with the other hand. In particular embodiments, the applicator allows for one-hand, one-motion administration. Moreover, the applicator eliminates the need to inject the animal, thereby increasing safety for both the animal and the person administering the vaccine.

The invention will now be described by the following set of non-limiting claims.

What is claimed is:

1. An applicator adapted to draw into and deliver a liquid composition to an animal per os, comprising:
   a resilient and/or elongated reservoir defining a longitudinal axis; and
   an elongate, hollow stem adapted to be inserted into the animal's mouth,
   wherein the stem comprises a proximal end operably connected to and in fluid communication with the reservoir,
   wherein the stem comprises a distal end adaptable to allow liquid to exit and enter the applicator,
   wherein the stem comprises a first stem region being along the longitudinal axis and a second stem region angled with respect to the longitudinal axis by an angle theta (Θ), which is from about 15 to about 35 degrees,
   wherein the first stem region and the second stem region have a length ratio in a range between 10:1 to 1:10, and
   wherein the applicator is adapted to sealably contain a carrier liquid of the liquid composition to be dispensed to the animal,
   wherein the distal end of the stem is further adaptable to deliver the carrier liquid to a vial containing a lyophilized immunogen such that the liquid composition is formed upon mixing of the carrier liquid with the lyophilized immunogen;
   wherein the distal end is further adaptable to retrieve at least some of the liquid composition from the vial; and
   wherein the applicator is adaptable to deliver at least a portion of the retrieved liquid composition to the animal to be vaccinated upon application of pressure to at least a portion of the applicator.

2. The applicator of claim 1, wherein the distal end comprises a frangible seal.

3. The applicator of claim 1, wherein theta is from about 20 to about 30 degrees.

4. The applicator of claim 3, wherein the range of the length ratio of the first stem region and the second stem region is between 5:1 to 1:5.

5. The applicator of claim 1, wherein theta is about 25 degrees.

6. The applicator of claim 1, wherein the range of the length ratio of the first stem region and the second stem region is between 5:1 to 1:5.

7. The applicator of claim 1, wherein the range of the length ratio of the first stem region and the second stem region is between 3:1 to 1:3.

8. The applicator of claim 1, wherein the range of the length ratio of the first stem region and the second stem region is between 2:1 to 1:2.

9. A kit comprising an applicator adapted to deliver a liquid composition to an animal per os and a vial of lyophilized immunogen, wherein the applicator comprises:

a resilient and/or elongated reservoir defining a longitudinal axis; and an elongate, hollow stem adapted to be inserted into the animal's mouth, wherein the stem comprises a proximal end operably connected to and in fluid communication with the reservoir, wherein the stem comprises a distal end adaptable to allow liquid to exit and enter the applicator, wherein the stem comprises a first stem region being along the longitudinal axis and a second stem region angled with respect to the longitudinal axis by an angle theta (Θ), which is from about 15 to about 35 degrees, wherein the first stem region and the second stem region have a length ratio in a range between 10:1 to 1:10, wherein the applicator is adapted to sealably contain a carrier liquid of the liquid composition to be dispensed to the animal, wherein the applicator comprises the carrier liquid;

wherein the distal end is adaptable to deliver the carrier liquid to the vial such that the liquid composition is formed upon mixing of the carrier liquid with the lyophilized immunogen;

wherein the distal end is further adaptable to retrieve at least some of the liquid composition from the vial; and wherein the applicator is adaptable to deliver at least a portion of the retrieved liquid composition to the animal to be vaccinated upon application of pressure to at least a portion of the applicator.

10. The kit of claim 9, wherein the distal end of the applicator comprises a frangible seal.

11. The kit of claim 10, wherein the applicator contains the carrier liquid, and the lyophilized immunogen is for admixing with the carrier liquid to form a blended vaccine or immunogen formulation.

12. The kit of claim 11, wherein the lyophilized immunogen induces immunity against influenza, parainfluenza, *bordetella*, rabies, parvovirus, adenovirus, or distempter.

13. The kit of claim 12, wherein the vial has a volume of 3 mL.

14. The kit of claim 9, wherein theta is from about 20 to about 30 degrees.

15. The kit of claim 14, wherein theta is about 25 degrees.

16. The kit of claim 15, wherein the applicator contains the carrier liquid, and the lyophilized immunogen is for admixing with the carrier liquid to form a blended vaccine or immunogen formulation.

17. The kit of claim 16, wherein the lyophilized immunogen induces immunity against influenza, parainfluenza, *bordetella*, rabies, parvovirus, adenovirus, or distempter.

18. The kit of claim 17, wherein the vial has a volume of 3 mL.

19. The kit of claim 14, wherein the applicator contains the carrier liquid, and the lyophilized immunogen is for admixing with the carrier liquid to form a blended vaccine or immunogen formulation.

20. The kit of claim 19, wherein the lyophilized immunogen induces immunity against influenza, parainfluenza, *bordetella*, rabies, parvovirus, adenovirus, or distempter.

21. The kit of claim 20, wherein the vial has a volume of 3 mL.

22. The kit of claim 9, wherein the range of the length ratio of the first stem region and the second stem region is between 5:1 to 1:5.

23. The kit of claim 22, wherein the range of the length ratio of the first stem region and the second stem region is between 3:1 to 1:3.

24. The kit of claim 23, wherein the range of the length ratio of the first stem region and the second stem region is between 2:1 to 1:2.

* * * * *